(12) United States Patent
Lusen et al.

(10) Patent No.: US 6,999,972 B2
(45) Date of Patent: Feb. 14, 2006

(54) SYSTEM FOR PROCESSING OBJECTS FOR STORAGE IN A DOCUMENT OR OTHER STORAGE SYSTEM

(75) Inventors: William D. Lusen, Ambler, PA (US); Bruce M. Flamma, Phoenixville, PA (US); Frank W. Racis, Spring City, PA (US)

(73) Assignee: Siemens Medical Systems Health Services Inc., Malvern, PA (US)

( * ) Notice: Subject to any disclaimer, the term of this patent is extended or adjusted under 35 U.S.C. 154(b) by 492 days.

(21) Appl. No.: 10/236,560

(22) Filed: Sep. 6, 2002

(65) Prior Publication Data

US 2003/0061229 A1    Mar. 27, 2003

Related U.S. Application Data

(60) Provisional application No. 60/318,106, filed on Sep. 8, 2001.

(51) Int. Cl.
*G06F 17/30* (2006.01)

(52) U.S. Cl. ............... 707/104; 707/10; 707/101; 707/102; 707/103

(58) Field of Classification Search .......... 707/102, 707/103, 104, 511, 3, 10, 101, 1, 5; 715/531; 382/305, 306
See application file for complete search history.

(56) References Cited

U.S. PATENT DOCUMENTS

| | | | |
|---|---|---|---|
| 4,008,956 A | 2/1977 | Stemmle | 355/8 |
| 5,070,531 A | 12/1991 | Schuerman et al. | 382/49 |
| 5,245,441 A | 9/1993 | Ruben | |
| 5,550,976 A | 8/1996 | Henderson et al. | |
| 5,608,541 A | 3/1997 | Yamada | 358/448 |
| 5,659,164 A | 8/1997 | Schmid et al. | 235/375 |
| 5,682,444 A | 10/1997 | Reasoner, Jr. et al. | |
| 5,685,003 A * | 11/1997 | Peltonen et al. | 715/531 |
| 5,864,863 A * | 1/1999 | Burrows | 707/103 R |
| 6,023,715 A | 2/2000 | Burkes et al. | 707/514 |
| 6,122,684 A | 9/2000 | Sakura | 710/73 |
| 6,181,837 B1 | 1/2001 | Cahill et al. | |
| 6,192,165 B1 | 2/2001 | Irons | |
| 6,427,032 B1 | 7/2002 | Irons et al. | |
| 6,442,748 B1 | 8/2002 | Bowman-Amuah | |
| 6,457,017 B1 * | 9/2002 | Watkins et al. | 707/103 R |
| 6,594,650 B1 | 7/2003 | Hasuo et al. | |
| 6,606,637 B1 * | 8/2003 | Hill et al. | 707/104.1 |
| 6,829,611 B1 | 12/2004 | Majewski et al. | |
| 2002/0065848 A1 * | 5/2002 | Walker et al. | 707/511 |
| 2002/0083079 A1 | 6/2002 | Meier et al. | 707/104.1 |
| 2002/0111960 A1 | 8/2002 | Irons et al. | |
| 2003/0135495 A1 * | 7/2003 | Vagnozzi | 707/3 |

FOREIGN PATENT DOCUMENTS

| | | |
|---|---|---|
| WO | WO 01/04571 A1 | 1/2001 |
| WO | WO 01/65354 A1 | 9/2001 |
| WO | WO 02/17136 A1 | 2/2002 |

* cited by examiner

*Primary Examiner*—Thuy N. Pardo
(74) *Attorney, Agent, or Firm*—Alexander J. Burke

(57) ABSTRACT

The invention is directed to a system for processing data to be stored in a document-imaging system that includes a posting processor programmed for receiving at least one object containing the data; a bursting processor programmed for bursting the object to create at least one bursted object; an index extraction processor programmed for extracting indexing information on the bursted object; and a communication processor programmed for transmitting the transformed bursted object and the indexing information to the document-imaging system. The invention may further include a transformation processor for transforming the bursted object and a user interface for configuring the system.

12 Claims, 5 Drawing Sheets

SYSTEM FOR PROCESSING OBJECTS FOR STORAGE IN A DOCUMENT OR OTHER STORAGE SYSTEM

This is a non-provisional application of provisional application Ser. No. 60/318,106 by W. Lusen et al. filed Sep. 8, 2001.

FIELD OF THE INVENTION

The present invention is related to a computerized system for processing objects to be stored in a document-imaging system. More particularly, the present invention is related to a computerized system that breaks objects apart and extracts indexing information for use in storing the objects in a document-imaging system.

BACKGROUND

Document-imaging systems are often used as a platform for the management of healthcare related documents and the integration of multimedia content in a client server environment. Such systems require tools for applications to acquire, store, organize, display and manage multimedia content (including traditional reports, images, voice, video, etc.). They also require an adequate mechanism to share multimedia content with all healthcare applications regardless of where the content originated.

Document imaging is often used for long-term storage of patient data and hospital information. This data is often received electronically from a clinical or financial system or it can be input from a paper format (e.g., scanning). Electronic data (in particular, demographic data) that is stored by the document-imaging system is often sent via electronic transactions from a third-party source. Inbound transactions from any external application are handled by a receiver application. Transactions are usually sent from the application to an interface engine, which then routes the transactions to the document-imaging system. The document-imaging system can receive Imaging Style Transactions, XML, or HL7 transactions. After a transaction has been received, the transaction is parsed and the database for the document-imaging system is updated. Outbound Transactions are similarly handled by a sending application.

The document-imaging platform is typically a combination of components, each of which has a specific purpose for storing, retrieving, and/or organizing binary objects (e.g., documents) in an archive. There is need for a component that can accept output from other systems and prepare it for storage in such a way that the content of the output is stored and organized for efficient retrieval.

Accordingly, a system is needed that is capable of accepting output from these different components and from external applications and prepare it for storage in a highly efficient manner.

SUMMARY OF THE INVENTION

The invention is directed to a system for processing objects to be stored in a document-imaging system that includes a posting processor programmed for receiving at least one object containing the data; a bursting processor programmed for bursting the object to create at least one bursted object; an index extraction processor programmed for extracting indexing information on the bursted object; and a communication processor programmed for transmitting the transformed bursted object and the indexing information to the document-imaging system. The invention may further include a transformation processor for transforming the bursted object and a user interface for configuring the system.

DETAILED DESCRIPTION

The invention will be understood more fully from the detailed description given below and from the accompanying drawings of the preferred embodiments of the invention; which, however, should not be taken to limit the invention to a specific embodiment but are for explanation and understanding only.

The document-imaging system within which the present invention is to be used stores multimedia content in the form of documents. A document in this context is preferably a single, self-contained, data object that is comprised one or more objects. Each object is typically a single binary file. Objects are typically text reports, scanned images, word processing documents, or any other binary data generated by any application.

The document-imaging system organizes documents by filing them hierarchically into folders using a relational database. A folder in this context is simply a virtual container for a set of documents that "belong" to a specific owner. This is analogous to a typical manila folder in a filing cabinet. Similarly, filing a document into a folder is analogous to inserting a paper document into a manila folder. An "owner" is a set of indexes that uniquely identify a specific person, organization, or entity. For example, a patient is a potential "owner" of documents relating to that patient's health care record.

Figure 1:
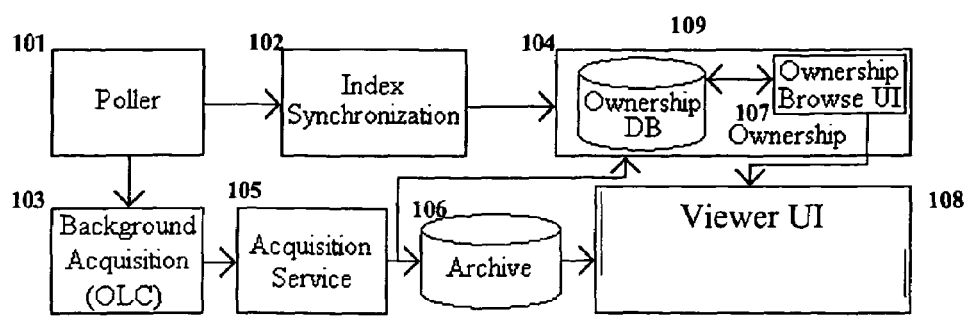
FIG. 1 is a diagram illustrating an overview of a document-imaging system incorporating the storage management system of the invention.

FIG. 1 illustrates a high-level overview of the functionally active components of a document-imaging system incorporating the present invention. The arrows show, in the simplest terms, how the active components relate to each other. Specifically, poller (101) detects new files to be stored or processed by the document-imaging system, and feeds them to index synchronization component (102) and/or to background acquisition component (103) depending on their contents. Index synchronization component (102) takes batched or real-time indexing information, for example, from data repository or database (109) containing a master patient index, interprets the indexing information, and passes it to ownership component (104) to create and/or update folder information.

Background acquisition component (103) processes files to be stored in the document-imaging system by breaking them apart into documents and extracting indexing information for them. These documents and their indexing information are then passed to acquisition service (105). Acquisition service (105) gathers new documents and their indexing information and routes them to storage manager (106) and to ownership component (104) so they are properly stored and associated with the correct folders. Storage manager (106) stores objects, organizes them into documents, and provides hierarchical storage management for the objects.

Ownership component (104) organizes documents by maintaining indexing information in the form of folders and also maintaining the list of documents in each folder within database (109). Ownership also preferably includes browser user interface (107), which is programmed to display, navigate, and maintain the hierarchy of folders and a summary of their contents. Browser user interface (107) is also preferably programmed to enable the display of selected documents by feeding them to the viewer user interface (108). Viewer user interface (108) renders document objects to an output device such as a screen or printer and allows navigation across multiple documents.

This document-imaging system thus preferably utilizes three types of data interfaces that are programmed to communicate with external applications to integrate multimedia content into their workflows and business processes. The interoperable user interfaces provide robust user forms (such as HTML or XML generated user input forms) that external applications may embed within their own user interface as a tightly integrated part of the application workflows. These forms relieve the application of the burden of understanding and formatting the complex multimedia information presented by the document-imaging system. Service level application interfaces use conventional data streams that represent the information stored in the document imaging system and to allow the system to intermix multimedia information with other data in the application. The background data exchange interfaces are programmed to provide communication points between the document-imaging system and an external application to share information therebetween. These interfaces are typically used by the document-imaging system to accept index information or to automatically acquire new documents.

The document imaging system preferably operates on a Microsoft Windows 2000 or Windows NT Server, although not limited thereto, and is described in that implementation herein. In this context, the present invention, as described in more detail below, preferably executes as an asynchronous service that is initiated by independent software (one example being the Poller (101)). This service is accessed preferably as a fully functional Web Service (as understood by anyone of ordinary skill in the art) or as a standard HTTP Post request using an XML as input. The Background Acquisition service is controlled by the calling software.

The present invention is directed to the background acquisition component of the above-described document-imaging system. Background acquisition component (103), otherwise known as an "On-Line Clerk" or "OLC," is programmed to acquire virtually any output electronically from virtually any application. The functionality of background acquisition component (103) is primarily two-fold: to provide non-interactive (i.e. no user involvement) interfaces (known as acquisition sources) for acquiring output and to provide enhanced manipulation of objects before they are stored and indexed.

Background acquisition component (103), with help from Poller component (102) is programmed to supports a plurality of acquisition sources. These include, for example, any output that can be transmitted via File Transfer Protocol (FTP), and any output that can be saved as files on a conventional network share.

For convenience, the pre-manipulated objects acquired from these sources are herein called "reports". Background acquisition component (102) is programmed to then manipulate these reports in at least the following ways. A report may be "Burst" into multiple objects if the report contains more than one document. This is analogous to bursting printed output when that printing is done or tractor fed paper. Bursted objects may be "Transformed" into one or more alternate objects if the original objects are in XML format. Indexes for these objects may be read either from an associated tag file or from the content of the objects themselves. A tag file is an ASCII file that contains pointers to non-ASCII files and their associated index information. All of these processes are configurable and controlled by processing rules, as discussed in more detail below.

Figure 2:
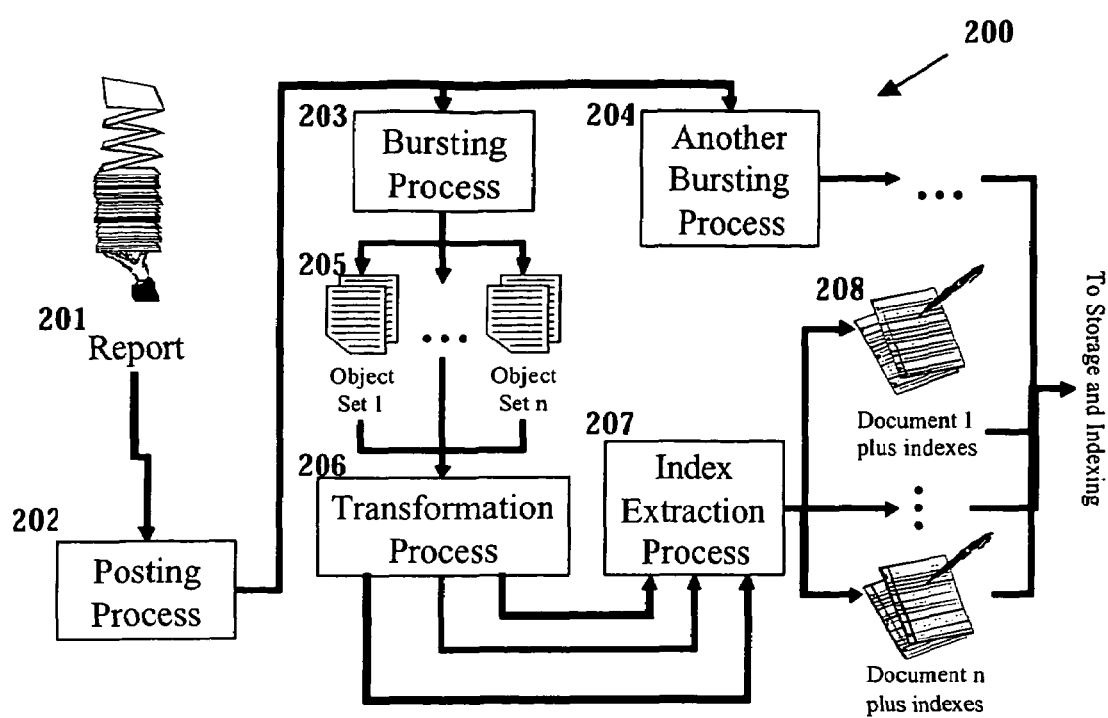
FIG. 2 is a diagram illustrating a preferred embodiment of the software process elements of the invention.

The preferred software elements of background acquisition component (103) process consists of several components are illustrated in FIG. 2. Of course, those of ordinary skill in the art will appreciate that this is simply a functional breakdown of the system and the document processor of the invention is not limited to any particular combination of these software elements. As shown in FIG. 2, reports (201) are posted to background acquisition process (200) using posting process (202), which is programmed to decide how many times a report will pass through the subsequent steps in the process. Posted reports are burst into one or more smaller objects (205) that are organized into subsets (the subsets are herein called documents) using bursting process (203). Bursted objects (205) may be "Transformed" (if they are in XML format) one or more times into actual objects that will be stored as distinct documents using transformation process (206). Indexing information may then be read from the report/objects by using index extraction process (207). The documents and their associated indexing information (208) are then passed on to other components of the document-imaging system that will manage the storage of those objects and their associated indexes.

Posting a report involves deciding how many times the report will pass through the burst/transform/index-extraction processes. The posting process maps the report's file name and/or extension to one or more report types. Each report type then preferably initiates a single processing pass for the report. The bursting/transformation/indexing processes (detailed below) then use each report type to configure how they will process the report during each pass. The mappings from report file names and/or extensions to report types are configured using posting rules that are programmed into the system in a conventional manner. These rules preferably contain string values that are compared with report file names and extensions and may include wild card characters.

The following is a preferred embodiment of the steps used to implement posting process (202):

1. Posting is initiated by a call to posting process (202). This call is preferably made using standard HTTP Post using XML streams for input.

2. The file name, extension, and hospital/region codes are extracted from the XML streams.

3. The file name, extension, and hospital/region codes are compared with string masks contained in the programmed posting rules to determine how many times to process the report (see discussion of posting rules below).

4. For each matching posting rule, bursting process (203) is called to control the processing of the report, which in turn calls transformation process (206), index extraction process (207), and the storage/indexing processes of the document imaging system.

The posting rules provide the mapping between a report and the number of times it will be processed. A posting rule preferably has the following attributes: ReportName, ReportExtension, HospRegion code, ReportType and Forced- HospRegion. In a preferred embodiment, the file name, extension, and hospital/region codes are compared with the posting rules based on the order and criteria shown in Table 1.

TABLE 1

| Precedence | ReportName | ReportExtension | HospRegion |
|---|---|---|---|
| 1 | Exists | Exists | Exists |
| 2 | Exists | Blank | Exists |
| 3 | Blank | Exists | Exists |
| 4 | Exists | Exists | Blank |
| 5 | Exists | Blank | Blank |
| 6 | Blank | Exists | Blank |
| 7 | Default | | |

A report may be qualified as multiple ReportTypes, which allows a single report to be passed to background acquisition component (103) once even though it is processed multiple times using different bursting/transformation/index extraction criteria. The ReportType is preferably used as input to bursting process (203) and the ForcedHospRegion is preferably used to override any entity or organization information when indexing.

As noted above, bursting a report is the process of breaking up the report into one or more smaller objects and organizing those objects into documents. The bursting process preferably reads the entire report and recognizes the beginning and end of each object to extract it. The rules that govern bursting process (203), i.e., bursting rules, map a report type to a document type that will be associated with each document stored. The rules also specify which bursting process type to use, and any details required to accomplish the specified type of bursting.

The following is a preferred embodiment of steps used to implement bursting process (203).

1. Bursting is initiated from posting process (202). The original information sent to posting is also available for bursting.

2. Bursting process (203) maps the report's ReportType to determine the bursting rules that will be used to process the report (see the discussion of bursting rules below for more information).

3. The bursting rules provide information about how to break up the report into objects and documents. There are preferably a number of different methods (known as bursting types) used to perform this task. The bursting rules also preferably contain any extra information required to configure the specific bursting type used (see the discussion of bursting types below for more information about the types and the extra information required to perform each bursting method).

4. If directed by the bursting rules, the report is sent through a pre-bursting preparation process that will facilitate the specified bursting method (see the discussion of pre-bursting preparation below).

5. If the report contains any header and/or trailer pages, they are removed and sent to index extraction process (207) to be read for "report level" indexes. These indexes are preferably saved so they may be used for all documents stored. The header and trailer pages may also be kept if they are to be reapplied to each extracted document.

6. The first document's objects are then extracted and sent to index extraction process (207) to be read for "report level" indexes. These indexes are saved so they can be used for all documents stored.

7. The first document's objects are then sent to index extraction process (207) for "document level" indexes. These indexes are used for the first document.

8. The first document's objects are then sent to other components of the document-imaging system to be stored and associated with the specified index values. These documents are stored as documents of the type specified by the bursting rules. If the bursting rules specify that the report is a Tag File, then the extracted object is used for indexing information and will not be stored. Instead, the object extracted from the report contains a reference (usually a file specification pointing to a separate file) to the actual object that will be stored. This is called Tag File Processing, which is discussed in more detail below in regard to the enhanced capabilities of the system. If the bursting rules specify that the report will be Ghost Posted (also discussed below), the objects are not sent for storage.

9. All subsequent objects are then extracted, grouped into documents, and iteratively and repetitively passed steps 7 and 8.

10. Each document's objects are sent to other components of the document-imaging system to be stored and associated with the specified index values.

The bursting rules provide the mapping between a report type (as specified by the posting rules) and how the report will be processed. A bursting rule preferably has the following attributes: ReportType (arbitrary name used as a link between posting rules and bursting rules), DocType (the document type that will be used for all documents extracted from the report), FileFmt (the file format of the report and it's resultant documents such as "text" or "XML"), BurstingType (the bursting method to be used for the bursting process), and other supporting information (different for each Bursting Type).

An example of a bursting rule is shown in Table 2.

TABLE 2

| ReportType | DocType | FileFmt | BurstingType | SupportingInfo |
|---|---|---|---|---|
| FACE | FACESHT | TXT | First Page Bursting | Comparative text to determine the first page of each document and where to find it on the page. |

The supporting information is different for each BurstingType. The following is a list of ways to perform the bursting process (known as bursting process types):

Constant Bursting—Break up a report into documents based on a fixed number of pages per document. PagesPerDoc is required as extra information for this bursting type.

Last Page Bursting—Break up a report into documents based on a text string that appears on the last page of each document at a specified location. Extra information needed by Last Page Bursting includes: the text string that delimits the last page, the length of the string to be extracted for comparison, and the position of the string on the last page.

First Page Bursting—Break up a report into documents based on a text string that appears on the first page of each document at a specified location. Extra information needed by First Page Bursting includes: the text string that delimits the first page, the length of the string to be extracted for comparison, and the position of the string on the first page.

Key Bursting—Break up a report into documents based on a string or number that appears on the each page of the document at a specified location. When the string or number changes, a new document is burst. Extra information needed by Key Bursting includes: the text string or number that delimits each page of the document, the length of the string or number to be extracted for comparison, and the position of the string or number on the page.

Variable Bursting—Enhance first page, last page and key bursting to use a variable element to locate delimiters instead of relying on them to always be in a consistent row/column location. The variable element can be identified using various index extraction capabilities. Table 3 lists which index extraction capabilities apply to each Bursting Type.

TABLE 3

| Index Extraction Method | Key | First page | Last page |
|---|---|---|---|
| Row/Column | X | X | X |
| Column | X | X | X |
| Fixed From String | X | N/A | N/A |
| Variable From String | X | N/A | N/A |
| Variable | X | N/A | N/A |
| Window | X | X | X |

A more detailed explanation on how these capabilities work and what extra information is needed to support them is discussed in connection with index extraction below.

XML Element Bursting—(a.k.a. XML Tag Bursting) Break up a report into documents based on an XML node within an XML hierarchy. Each document is made up of an instance of the desired node and the elements and attributes it contains. The extra information needed for this type of bursting is the XML XPath that specifies the node that will be the root of each extracted document.

Bulk Bursting—Assume that the whole report is a document. No extra information is needed.

Bypass Bursting—Discard the whole report. No extra information is needed.

Bursting process (203) is further preferably programmed with the following enhanced capabilities:

Pre-bursting Preparation—Repaginate a report that does not contain form feeds or does not break on a key. This is in preparation for one of the above bursting processes. There are preferably two types of pre-bursting: fixed line and non-page. During fixed line pre-bursting, a form feed character is inserted after every nth line. This is preferably used on a report when it has no form feed characters. During non-page pre-bursting, all existing form feeds are removed and then re-insert based on some criteria. This is preferably used on a report when there are single pages in the report that are to be burst into multiple objects (usually because one printed page has data for multiple owners). In both cases, the report is simply read in and written back out with the form feed characters moved or inserted. The written version is then preferably used for the Bursting/Transformation/Indexing processes.

Header and Trailer Pages—Perform special processing with the report's header and trailer pages. Either they may be ignored (not stored at all) or they may be added to documents extracted from the report. This processing may be done on reports with either a fixed or variable number of header and trailer pages. To perform this processing, certain extra information is needed. For example, to strip away a fixed number of header pages the actual number of pages is needed. Bursting process (203) is preferably programmed to assume that the first document begins after passing that many pages. To strip away a fixed number of trailer pages the actual number of pages is needed. Bursting process (203) is preferably programmed to remove that many pages from the end of the report before processing it. To strip away a variable number of header pages a delimiter (a string for comparison purposes) on the last header page or the first page of the first document may be used to determine that all header pages have been passed. The extra information needed for this includes the string to compare, the length of the string to extract from the report for comparison, and the position to expect that string in the report. To strip away a variable number of trailer pages a delimiter (a string for comparison purposes) on the last page of the last document or the first trailer page may be used to determine that all documents have been extracted. The extra information needed for this includes the string to compare, the length of the string to extract from the report for comparison, and the position to expect that string in the report.

Ignoring Carriage Returns and Line Feeds near Form Feeds—Ignore carriage return characters and line feed characters when they either precede or follow a form feed character. This normalizes the number of lines on a page to facilitate the above bursting processes. The extra information needed for this is a switch indicating whether or not to ignore these characters.

Tag File Support—Each page of the report is not the page that will be stored. Instead each page contains a reference (usually in the form of a file name) to the actual file/object that will be stored as the archived page. Normal bursting processes are used on the tag file to determine how to group the pages into documents. The extra information needed for this is a switch indicating that the burst report is actually a tag file. The tag file then contains the name of the actual objects to store.

Ghost Posting—Use the bursting and index extraction capabilities of background acquisition component (103) to update owner indexes without extracting and storing any documents from the report. The extra information needed for this is a switch indicating that this is the desired processing. Bursting process (203) is programmed to use this information in deciding whether NOT to store the objects and call the indexing system with updated information.

Report Backoff—Delete all documents related to a report that partially processed due to errors. An administrative user or support person may preferably launch this program capability manually after investigating the reason for the errors and correcting them. Bursting process (203) keeps a record of the activity associated with bursting a report and then uses that information to delete all documents that were stored before the error occurred.

Transformation process (206) is preferably implemented for reports in XML format. In the preferred embodiment of the document processor, each page (extracted using XML Element Bursting) is transformed one or more times using XSL Style Sheets to produce one or more actual objects (each stored in a separate document). Each of these transformations may be used to create documents of different types.

Transformation rules that govern transformation process (206) preferably map a report type to one or more document types each with an associated XSL style sheet to transform the original extracted page into an actual page to be stored.

The following is a preferred embodiment of steps used to implement transformation process (206):

1. Bursting process (203) initiates transformation process (206) when one or more transformation rules exist for the report type. The specified transformations are preferably applied to each object extracted from the report immediately after it is extracted.

2. An extracted object is transformed (preferably using industry standard XML/XSL transformation) once for each transformation rule specified.

3. Each transformation changes the original object into a new object that is then sent to index extraction process (207) that is subsequently stored as a document of a type specified by the transformation rule and associated with the extracted indexes. This may result in multiple documents being created from each object extracted from the report.

The transformation rules provide the mapping between a report type (as specified by the posting rules) and a set of transforms that are preferably applied to each object extracted from reports of that type. A transformation rule has the following attributes: ReportType (arbitrary name used as a link between posting rules and bursting rules), NewDocType (the document type that will be used for all documents created as a result of the specified transform), and an XslFileName (the actual transform to apply to each XML object extracted from the report). Sample transformation rules for a single ReportType are shown in Table 4.

TABLE 4

| ReportType | NewDocType | XslFileName |
|---|---|---|
| PTREG | FACESHT | PtRegDataToFaceSheet.xsl |
| PTREG | PTHIST | PtRegDataToPatientHistory.xsl |
| PTREG | INCIDENT | PtRegDataToIncidentReport.xsl |

For documents resulting from the bursting of a report, index values should be determined for each document by indexing process (207). These index values may apply to the document itself, such as the document date or type, or they may apply to target owner folders with which the document will be associated. An owner folder represents a patient or other object that can contain or "own" documents.

The index extraction rules that govern the extraction and valuing of indexes during the processing of a report preferably map the report's associated document type and file format to actual indexes. Each rule also includes information about the format of the index (such as text, date, numeric, etc.) and any adjustment that is to be made to extracted data before valuing the index.

The following is a preferred embodiment of steps used to implement index extraction process (207).

1. Bursting process (203) initiates index extraction process (207) for each object bursted (after the object is transformed if applicable).

2. Index extraction process (207) maps the target document's type, along with its file format, to determine what indexes to extract and how to extract them.

3. The index extraction rules provide information about how to find, read and format each index. There are preferably a number of different methods used to perform this task. The index extraction rules also contain any extra information required to configure the specific index extraction method used, which is described in more detail below.

4. Each index is preferably extracted from the object and merged with other extracted indexes into a single XML stream. This is done preferably by specifying an XML XPath for each index that will be valued with the extracted data.

5. Once all indexes have been extracted, the resultant XML stream is preferably returned to bursting to be merged with other indexes and used to identify and organize the stored document(s).

The index extraction rules provide a mapping from a target document's type and file format to a set of indexes and how to read the data used to value those indexes. It also determines the type of the index (i.e. will it apply to the document or to the document's target owner(s) and when to extract it (i.e. once during the processing of the report or every time a document is extracted from the report. An index extraction rule preferably has the following attributes: DocType (the type that will be assigned to the newly stored document), FileFmt (the file format of the document such as TEXT or XML), OwnerType (the type of owner that will be associated with the new document—if no value is assigned to this field then the index is to be applied directly to the document, not to it's owner folders), IdxLevel (the index level of the index such as "report wide" or "document specific"—see the discussion of index levels below for more detail), IdxXPath (the XPath of the index that will be valued with the extracted data in the merged XML stream), ExtractType (the method used to extract the index data—see Index Extraction Methods below for more detail), IdxPart (a sequence number indicating that the data extracted using this rule will be concatenated with data extracted using other rules to create a single index value), IdxDefVal (a default value to be assigned to the index if no data is found on the report), and other supporting information (different for each index extraction). Sample index extraction rules for a single DocType/FileFmt are shown in Table 5.

TABLE 5

| DocType/ FileFmt | Owner Type | Extract Type | IdxXPath and SupportingInfo |
|---|---|---|---|
| FACESH T/TXT | Encounter | Variable | XPath: Owner[@OwnerTypeName= 'Encounter']/EncNo SupportingInfo: Comparative text to determine the first page of each document and where to find it on the page. |
| FACESH T/TXT | Encounter | Variable | XPath: Owner[@OwnerTypeName= 'Encounter']/EncStartDate SupportingInfo: Comparative text to determine the first page of each document and where to find it on the page. |
| FACESH T/TXT | Encounter | Variable | XPath: Owner[@OwnerTypeName= 'Encounter']/Owner[@Owner TypeName='MedRec']/MedRecMRN SupportingInfo: Comparative text to determine the first page of each document and where to find it on the page. |
| FACESH T/TXT | | Variable | XPath: DocDateTime SupportingInfo: Comparative text to determine the first page of each document and where to find it on the page. |

The supporting information is preferably different for each extract type and is described below for each method.

The combination of DocType and FileFmt is used to map index extraction rules so that two reports resulting in documents of the same type (e.g. a patient bill) can be processed differently based on the format of its content (e.g. indexes are extracted from a TEXT report using different techniques than indexes extracted from an XML formatted report).

There are preferably two types of indexes valued by the index extraction process: document indexes and owner indexes. Document indexes are indexes that apply to the actual document(s) being stored such as the document date, create date/time, status, etc. Owner indexes are indexes that apply to the owner(s) in which a document will be filed. The "Owner Type" attribute of the index extraction rule specifies what the index's type will be. If the owner type is valued, the index is an owner index; otherwise, it is a document index.

An index level refers to when an index value is extracted and for which document or documents that index will apply. There are preferably two index levels supported by background acquisition component (103): report and document. Report level indexes index values that apply to every document extracted from a report or for every document's owner(s). Below is a sample list of ways to value report level indexes:

Rule Defaulted Index—An index assigned a pre-determined value by the index extraction rule.

Passed Index—An index valued from information passed into the background acquisition component (103), either from Poller (102) or from an application calling background acquisition component (103) directly. This information generally comes from the XML streams passed into posting process (202).

Header/Trailer Index—An index valued from information extracted from the header and/or trailer pages of a report.

First Document Index—An index valued from information extracted from the first document burst from a report.

Document level indexes index values that apply to the current document being stored or to that document's associated owner(s). These indexes are preferably valued using information extracted from the document being stored.

The following is a list of preferred index extraction methods programmed into index extraction process (207):

No Extraction—No value is extracted. Date indexes may be valued to today's date while all other indexes are explicitly set to no value. The extra information needed for this index extraction method is a switch indicating whether or not to use "today's date" to value the index if and if the index is a date field.

Row/Column Extraction—Extract the index from the document based on a fixed set of coordinates. The extra information required for this method includes the page on which the index may be found (relative to the document being extracted), the line (a.k.a. row) and column on that page where the index may be found and the length of the index (i.e. the number of characters to read).

Column Extraction—Search down a column until a valid index is found and then extract that index. Extra information for this method includes: the column in which to search for the index, the page on which the index may be found (relative to the document being extracted), the length of the index (number of characters to be read), the minimum number of digits if the index is a numeric fields, and/or the date format if the index is a date field.

Fixed From String Extraction—Search for a specified string then extract the data at a specified offset from the string. Extra information for this method includes: the page on which the index may be found (relative to the document being extracted), the string to search for, the distance (or offset) in characters from the string to the actual index data, the expected date format (if the index is a date field), the minimum number of digits required (if the index is a numeric field), and the length of the index (number of characters to be read).

Variable From String Extraction—Search for a specified string then extract the data at a variable offset from the string. Extra information for this method includes: the page on which the index may be found (relative to the document being extracted), the string to search for, the expected date format (if the index is a date field), the minimum number of digits required (if the index is a numeric field), and the length of the index (number of characters to be read). Date and numeric indexes are supported by this method.

Variable Extraction—Search for either a date or a numeric from the beginning of the object and extract it. Extra information for this method includes: the page on which the index may be found (relative to the document being extracted), the expected date format (if the index is a date field), the minimum number of digits required (if the index is a numeric field), and the length of the index (number of characters to be read). The whole page is searched until a valid index is found or the end of the page is reached. Date and numeric indexes are preferably supported by this method.

From Previous Index Extraction—Extract an index located at an offset from a previously found index. Extra information for this method includes: the page on which the index may be found (relative to the document being extracted), the row offset (i.e. the number of rows to move) from the previous index, the fixed column to find the index data (NOT an offset from the previous index), the expected date format (if the index is a date field), the minimum number of digits required (if the index is a numeric field), and the length of the index (number of characters to be read). It is common to use multiprocessing (discussed below) with Extract from Previous Index but the two are functionally independent.

XML Element Extraction—(a.k.a. XML Tag Extraction) Search an XML document for nodes specified by an XML XPath. The extra information for this method is the XPath of the XML tag that contains the index data.

Window Extraction—Search a row/column window until a valid index is found then extract that index. Extra information for this method includes: the page on which the index may be found (relative to the document being extracted), the row/column window in which to look for the index (the minimum line and column to the maximum line and column), the expected date format (if the index is a date field), the minimum number of digits required (if the index is a numeric field), and the length of the index (number of characters to be read). Date and numeric indexes are preferably supported by this method.

Default Extraction—Assign a specific default value to an index. Nothing is extracted from the document. If the index is a facility/entity identifier then the value is assigned based on either what's passed in to the Posting process via the Origin stream or by a configuration parameter that maps the report name to a specific facility/entity identifier; otherwise, the value to be assigned is taken from extra information in the index extraction rule.

Index extraction process (207) is preferably programmed with the following enhanced capabilities:

Ignoring Carriage Returns and Line Feeds near Form Feeds—Ignore carriage return characters and line feed characters when they either precede or follow a form feed character. This has the advantage that it normalizes the number of lines on a page to facilitate the specification of "Row" and "Line" values in the above index extraction methods.

Multiprocessing—Associate a document with more than one instance of an owner whose type is specified by the filing rules in ownership component (104). For example, a single document may contain data for many patients. The filing rules would specify that documents of that type should be filed to an encounter folder. This document would be filed to the encounter folder for every patient listed in the document.

Data Adjustment—Manipulate extracted data before assigning it as a value to an index. Below is a list of ways that extracted data can be manipulated.

No Adjustment—Assign the data to an index as extracted. This is a simple assignment.

Numeric Adjustment—Eliminate leading and trailing whitespace (e.g. spaces, tabs, etc.) then validate the data as a string of digits. This can be enhanced further to include Self Check Digit (SCD) validation which involves using the last digit as a checksum value calculated using modulo arithmetic on the preceding digits (the types of modulo arithmetic that are possible include simple modulo-10, simple modulo-11, and a modified modulo-11 where the potential resultant value of 10 is configurably mapped to a different digit but is usually zero).

Date Adjustment—Validate the data as a date then normalize according to configurable parameters. Possible normalizations may include none (i.e., do not change the date in any way), normalize to beginning of the extracted date's week (this involves changing the date to the first day of the week in which the date falls—note that the first day of the week is configurable), normalize to a specific day of the extracted date's month (this involves changing the date to a specific date of the month in which the date falls—this is usually the first of the month but this is configurable), and normalize to the first day of a specified month of the extracted date's year (this involves changing the date to the first day of a month of the year in which the date falls—the month is usually January but this is configurable).

Literal Month Adjustment—Validate the data either using Date Adjustment or as a numeric between 1 and 12 (with a possible adjustment of +/− some number of months) then convert the data to the name of the represented month in string format.

Text Adjustment—Justify and pad the data according to configurable parameters. Possible justifications are: none, right, or left. Possible paddings are: none, precede with zeros, or add spaces. This preferably applies if the length of the string index is fixed and the data is less than that length. A padding type of "precede with zeros" should be accompanied by right justification. A padding type of "add spaces" may be used with right or left justification (where the spaces are added to the beginning if the index is right justified and added to the end if the index is left justified). For ease of implementation, padding types of "none" and "add spaces" are essentially synonymous for right and left justification.

Mapping—Change the data from the extracted value to another literal value based on some criteria applied to the extracted value. Multiple mappings may be specified for an index and the mappings are preferably defined in one of two ways: change the data value to the mapped value if the extracted value matches the specified text mask, or change the data value to the mapped value if the extracted value does NOT match the specified text mask. The text masks and their mapped values are specified in the index extraction rules. For a given index, the matching mappings should all be checked first, followed by a single not matched mapping.

Once all objects for a document have been burst from the report and the indexes have been valued for the document and intended target owners, background acquisition component (103) sends all of the information to other components of the document-imaging system so they can be stored and associated with the proper indexing information. This is preferably done in a conventional manner such as by calling application programming interfaces (API's) implemented by those other components and can be configured to occur conditionally.

Background acquisition component (103) preferably integrates with external applications and with users by using an asynchronous service that takes a report along with information regarding the origin of the request, initial values for document indexes, and possibly an explicit specification of the owner (or owners) to which the extracted documents are to be filed. Applications and systems that call posting process (202) are themselves considered acquisition sources. This service is exposed for public use via an HTTP request made to the document-imaging system web server (preferably running on Windows 2000 or higher and using Microsoft Internet Information Server, although not limited thereto. This HTTP request preferably uses standard HTTP-Post with an XML stream as input. All acquisition sources that feed background acquisition component (103) are preferably implemented using Poller (102). They are asynchronous and involve interfaced data exchange rather than direct service integration.

Figure 3A:
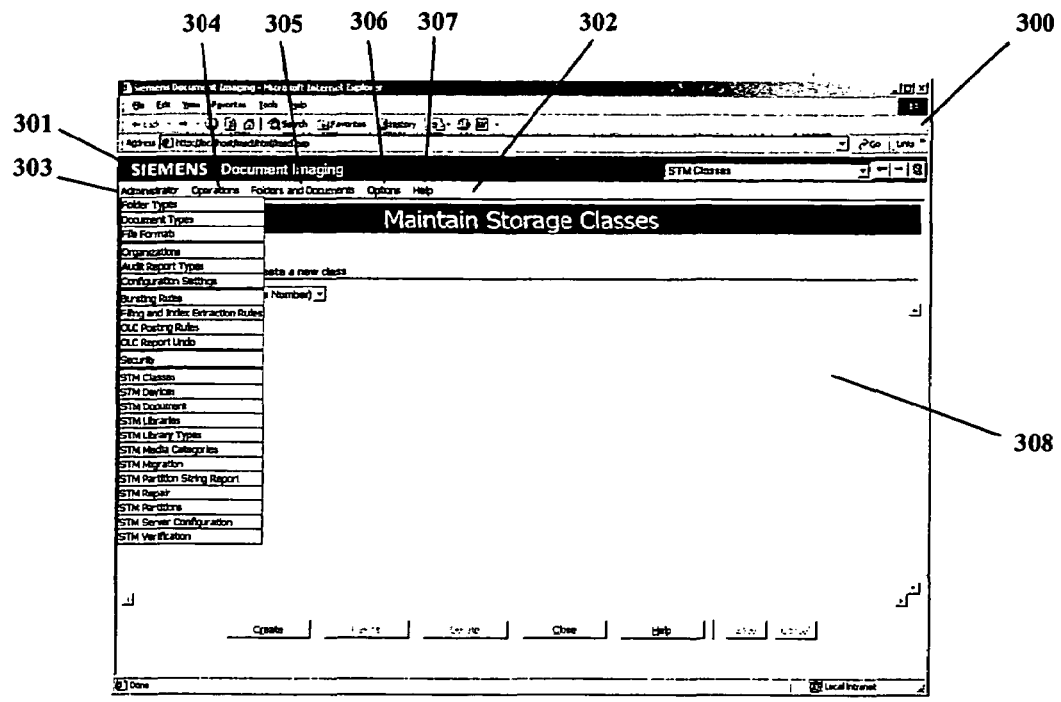
FIGS. 3(a)–(c) are a computer screenshots of a management user interface screen in accordance with aspects of the invention.

User interface (108) contains a set of interfaces that are programmed to allow administrators and support personnel to define, configure, and manage the document processor. An example of how these interfaces may be configured is described in more detail below in connection with FIGS. 3(a)–(b). FIG. 3(a), is a computer screenshot illustrating the user interface (300) to the document-imaging system. As shown in FIG. 3(a), the user interface may operate as a plug-in viewer to an Internet Web browser (301), such as Microsoft's Internet Explorer (although not limited thereto). User interface (300) may include tool bar (302), having administrator menu (303), operations menu (304), folder and documents menu (305), options menu (306), and help menu (307).

Administrator menu (303) has been expanded to show all available administrative options for the document imaging system. All of the menu items for the document processor appear between "Configuration Settings" and "Security" on administrator menu (303).

Figure 3B:
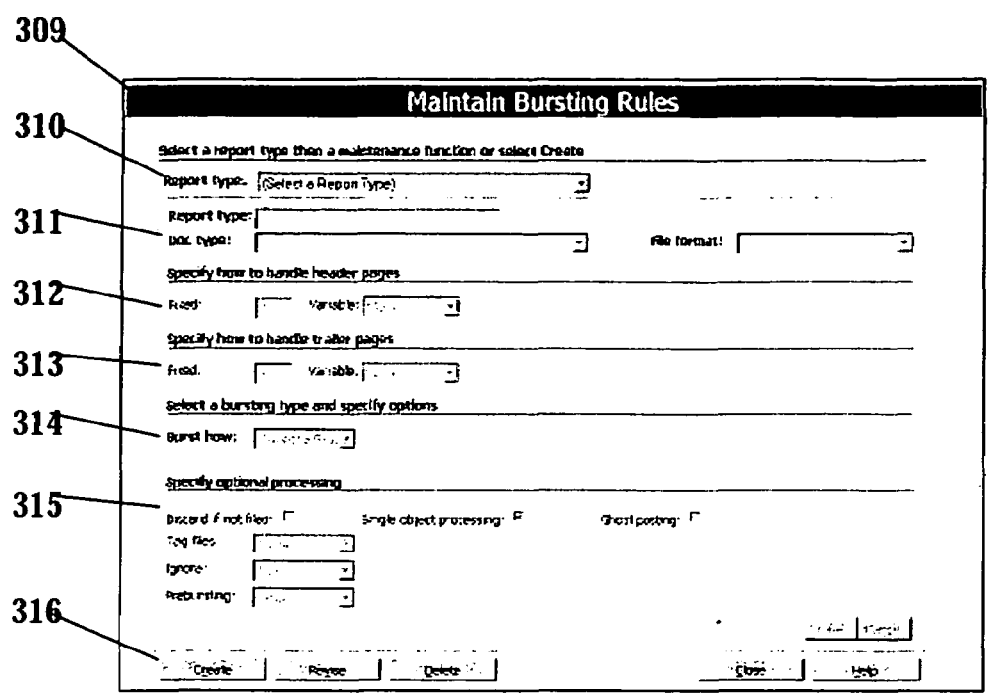

To set up a bursting rule, the user selects the "Bursting Rules" option on administrator menu (303). The Maintain Bursting Rules window (309) appears, which is illustrated in FIG. 3(b). The Maintain Bursting Rules screen serves two interrelated purposes. First, it provides the means by which background acquisition component (103) associates the report type to the bursting rule. Next, it identifies how to break the report up into pieces.

As shown in FIG. 3(b), the administrator may use Maintain Bursting Rules window (309) to configure all of the bursting rule criteria discussed above, including specifying the report type (310) along with the document type and file format (311), specifying how to handle header pages (312), specifying how to handle trailer pages (313), selecting a bursting type and specifying its options (314), and specifying how to handle optional processing. The administrator may create, revise, save, and delete a rule by selecting the appropriate button (315).

Figure 3C:
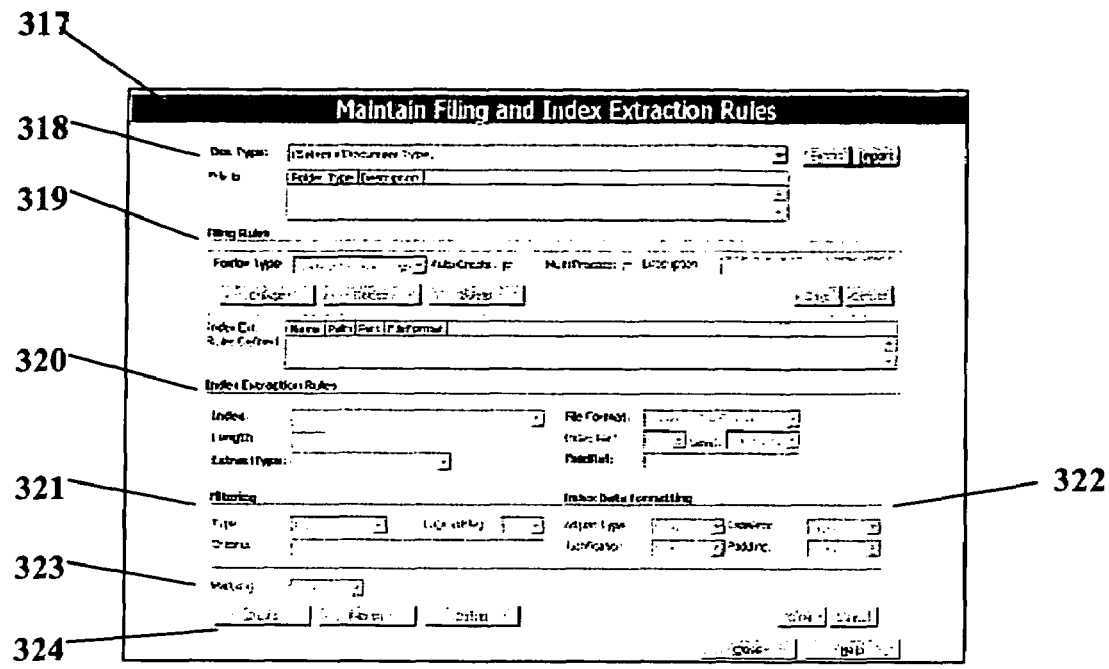

The administrator may configure the index extraction rules in a similar manner by selecting "Filing Index Extraction Rules" from administrator menu (303). The Maintain File and Index Extraction Rules window (317) appears, which is illustrated in FIG. 3(c). The administrator may select the document type (318), the filing rules (319), the specifics of the index extraction rule (320), filtering (321), index data formatting (322), and mapping (323). As with the bursting rules, the user may create, revise, save, and delete the index extraction rules using buttons (324).

Although this invention has been described with reference to particular embodiments, it will be appreciated that many variations will be resorted to without departing from the spirit and scope of this invention as set forth in the appended claims. For example, the terms "computer", "computer system", or "server" as used herein should be broadly construed to include any device capable of receiving, transmitting and/or using information including, without limitation, a processor, microprocessor or similar device, a personal computer, such as a laptop, palm PC, desktop, workstation, or word processor, a network server, a mainframe, an electronic wired or wireless device, such as for example, a telephone, an interactive television, such as for example, a television adapted to be connected to the Internet or an electronic device adapted for use with a television, a cellular telephone, a personal digital assistant, an electronic pager, a digital watch and the like. Further, a computer, computer system, or system of the invention may operate in communication with other systems over a communication network, such as, for example, the Internet, an intranet, or an extranet, or may operate as a stand-alone system.

What is claimed is:

1. A system for processing an input document for storage, comprising:
   an input processor for receiving an input document;
   a document processor for dividing said input document to create one or more objects and for organizing said one or more objects into output documents;
   an index extraction processor for adaptively extracting indexing information associated with said one or more objects using a process selected in response to an object specific attribute; and
   a communication interface for providing an output of said output documents and said indexing information wherein
   said document processor, examines said input document to identify input document type and divides said input document to create one or more objects and organizes said one or more objects into said output documents using predetermined rules selected based on said identified input document type and
   said index extraction processor extracts and merges indexing information associated with a plurality of created objects to create an index for at least one of said output documents.

2. The system of claim 1, further comprising
   a transform processor for conditionally transforming said one or more objects into alternative objects.

3. The system of claim 1, wherein
   said index extraction processor identifies an object specific attribute associated with a particular object including at least one of, (a) document type identification information and (b) file format identification information, and uses said object specific attribute to select a process for extracting indexing information associated with said particular object.

4. A system for processing an input document for storage, comprising:
   an input processor for receiving an input document;
   a document processor for dividing said input document to create one or more objects and for organizing said one or more objects into output documents;
   an index extraction processor for adaptively extracting indexing information associated with said one or more objects using a process selected in response to an object specific attribute; and
   a communication interface for providing an output of said output documents and said indexing information wherein
   said index extraction processor identifies an object specific attribute associated with a particular object including at least one of, (a) document type identification information and (b) file format identification information, and uses said object specific attribute to select a process for extracting indexing information associated with said particular object.

5. The system of claim 4, wherein
   said document processor organizes said one or more objects by accumulating objects of said one or more objects having said desired output document characteristics into a particular target output document.

6. A system for processing an input document for storage, comprising:
   an input processor for receiving an input document;
   a document processor for dividing said input document to create one or more objects and for organizing said one or more objects into output documents;
   an index extraction processor for adaptively extracting indexing information associated with said one or more objects using a process selected in response to an object specific attribute; and
   a communication interface for providing an output of said output documents and said indexing information wherein
   said document processor iteratively divides and organizes a document in response to document type identification information and
   said index extraction processor identifies and extracts indexing information associated with said input document as a first index and indexing information associated with an object derived from said input document as a different second index.

7. A method of processing an input document for storage comprising the steps of:
   receiving an input document;
   dividing said input document to create one or more objects and for organizing said one or more objects into output documents;
   adaptively extracting indexing information associated with said one or more objects using a process selected in response to an object specific attribute;
   examining said input document to identify input document type and dividing said input document to create one or more objects and organizing said one or more objects into said output documents using predetermined rules selected based on said identified input document type;
   extracting and merging indexing information associated with a plurality of created objects to create an index for at least one of said output documents; and
   providing an output of said output documents and said indexing information.

8. The method of claim 7, further comprising
   the step of conditionally transforming said one or more objects into alternative objects and including the step of adaptively identifying and extracting indexing information associated with said alternative objects.

9. The method of claim 7, further comprising the steps of,
   identifying an object specific attribute associated with a particular object including at least one of, (a) document type identification information and (b) file format identification information, and using said object specific attribute to select a process for extracting indexing information associated with said particular object.

10. A method of processing an input document for storage comprising the steps of:
- receiving an input document;
- dividing said input document to create one or more objects and for organizing said one or more objects into output documents;
- adaptively extracting indexing information associated with said one or more objects using a process selected in response to an object specific attribute wherein
- said indexing information includes at least one of (a) document type identification information and (b) file format identification information, for use in identifying desired output document characteristics and including the steps of,
- identifying an object specific attribute associated with a particular object including at least one of, (a) document type identification information and (b) file format identification information, and using said object specific attribute to select a process for extracting indexing information associated with said particular object.

11. The method of claim 10, further comprising
the step of organizing said one or more objects by accumulating objects of said one or more objects having said desired output document characteristics into a particular target output document and including the step of
- adaptively identifying and extracting indexing information associated with said input document as a whole differently from indexing information associated with an individual object.

12. The method of claim 10, further comprising
the step of iteratively dividing and organizing a document in response to document type identification information.

* * * * *